United States Patent
Schrems et al.

(10) Patent No.: US 9,346,779 B2
(45) Date of Patent: May 24, 2016

(54) METHOD FOR PRODUCING DEHYDRO ROSE OXIDE

(71) Applicant: BASF SE, Ludwigshafen (DE)

(72) Inventors: Marcus G. Schrems, Ludwigshafen (DE); Jan Eggert, Meckenheim (DE); Jan U. Müller, Mannheim (DE); Jan-Dirk Arndt, Mannheim (DE); Günter Gottwald, Mannheim (DE); Volker Hütt, Hockenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/889,541

(22) PCT Filed: May 15, 2014

(86) PCT No.: PCT/EP2014/060003
§ 371 (c)(1),
(2) Date: Nov. 6, 2015

(87) PCT Pub. No.: WO2014/184311
PCT Pub. Date: Nov. 20, 2014

(65) Prior Publication Data
US 2016/0096814 A1    Apr. 7, 2016

(30) Foreign Application Priority Data
May 16, 2013   (EP) .................................. 13168094

(51) Int. Cl.
*C07D 309/04*   (2006.01)
*C07D 309/18*   (2006.01)
*B01J 31/02*    (2006.01)

(52) U.S. Cl.
CPC ........... *C07D 309/18* (2013.01); *B01J 31/0225* (2013.01)

(58) Field of Classification Search
CPC ............................ C07D 309/04; C07D 309/18
See application file for complete search history.

(56) References Cited

U.S. PATENT DOCUMENTS 4,429,144 A      1/1984   Hoffman
8,546,591 B2 *  10/2013   Koenigsmann et al. ...... 549/356

FOREIGN PATENT DOCUMENTS

| EP | 0082401 A1 | 6/1983 |
| EP | 1493737 A1 | 1/2005 |
| GB | 2036004 A | 6/1980 |
| SU | 825528 A1 | 4/1981 |
| WO | WO-79/00509 A1 | 8/1979 |
| WO | WO-2009/077550 A1 | 6/2009 |

OTHER PUBLICATIONS

International Search Reprot for PCT/EP2014/060003 mailed Jun. 17, 2014.
International Preliminary Report on Patentability for PCT/EP2014/060003 dated Nov. 17, 2015.
Tyman et al., "The reaction of 3-alkene-1-ols with aldehydes: a synthesis of (+-)-cis-2-)2'methyl-1'-propenyl)-4-methyltetrahydropyran", Tetrahedron Letters, vol. 51, pp. 4507-4508 (1970).

* cited by examiner

*Primary Examiner* — Sun Jae Yoo
(74) *Attorney, Agent, or Firm* — Drinker Biddle & Reath LLP

(57) ABSTRACT

The present invention relates to a method for producing dehydro rose oxide by reacting isoprenol and prenal in the presence of at least one sulfonic acid of formula $R^1$—$SO_3H$ as catalyst, wherein $R^1$ is selected from phenyl which carries 2 or 3 $C_1$-$C_4$-alkyl substituents, phenyl which carries one $C_8$-$C_{20}$-alkyl substituent and optionally also 1 or 2 $C_1$-$C_4$-alkyl substituents, and naphthyl which optionally carries 1 or 2 $C_1$-$C_4$-alkyl substituents.

16 Claims, No Drawings

METHOD FOR PRODUCING DEHYDRO ROSE OXIDE

CROSS-REFERENCE TO RELATED APPLICATIONS

This application is a national stage application (under 35 U.S.C. §371) of PCT/EP2014/060003, filed May 15, 2014, which claims benefit of European Application No. 13168094.4, filed May 16, 2013, both of which are incorporated herein by reference in their entirety.

The present invention relates to a method for producing dehydro rose oxide.

Dehydro rose oxide (4-methylene-2-(2-methylprop-1-enyl)-tetrahydropyran) is an important intermediate in the production of rose oxide. Rose oxide (2-(2-methylprop-1-enyl)-4-methyltetrahydropyran) in turn, especially the cis isomer, is a valuable aroma chemical used in the perfume industry, mostly in cosmetic products and detergents.

Dehydro rose oxide is generally synthesized by reacting 3-methylbut-3-en-1-ol (isoprenol) and 3-methylbut-2-enal (prenal) under acidic conditions.

J. H. P. Tyman at al. describe in Tetrahedron Lett. 1970, 51, 4507-4508 the reaction of 3-methyl-2-buten-1-al and 2-methyl-1-buten-4-ol to the corresponding 4-methylene-tetrahydropyran. The reaction is said to be carried out similarly to the reaction of 3-methylbutanal with 2-methyl-1-buten-4-ol, which in turn is said to be carried out under acidic conditions. Further details are not disclosed.

WO 79/00509 and EP-A-0082401 relate to the preparation of cis-rose oxide by hydrogenation of dehydro rose oxide. The latter is in turn said to be prepared as described in the above article by Tyman et al.

There is a constant need for improving the common processes for preparing dehydro rose oxide, as the yields are not yet satisfactory, and, moreover the by-product nerol oxide, a double bond isomer of dehydro rose oxide, is formed in rather high amounts, which is problematic as its separation s laborious.

DETAILED DESCRIPTION OF THE INVENTION

The object of the present invention was therefore to provide a method for the production of dehydro rose oxide which results in higher yields of the desired product and a reduced formation of nerol oxide. Moreover, preferably, the catalyst used in this process should not interfere negatively in the process, i.e. it should be easy to handle, especially easy to introduce and remove, and should not Interfere negatively with the reactors in which the reaction is generally carried out on a technical scale.

Surprisingly it was found that this object is achieved if sulfonic acids are used as catalysts.

Thus, the invention relates to a method for producing 4-methylene-2-(2-methylprop-1-enyl)-tetrahydropyran (dehydro rose oxide) of formula I

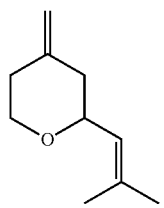

which method comprises reacting 3-methylbut-3-en-1-ol (isoprenol) of formula II and 3-methylbut-2-enal (prenal) of formula III

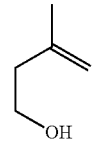

(II)

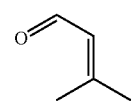

(III)

in the presence of at least one sulfonic acid of formula $R^1$—$SO_3H$ as a catalyst, wherein $R^1$ is selected from phenyl which carries 2 or 3 $C_1$-$C_4$-alkyl substituents, phenyl which carries one $C_8$-$C_{20}$-alkyl substituent and optionally also 1 or 2 $C_1$-$C_4$-alkyl substituents, and naphthyl which optionally carries 1 or 2 $C_1$-$C_4$-alkyl substituents.

"At least one sulfonic acid" means that a single sulfonic acid or a mixture of different sulfonic acids can be used. Especially high molecular weight sulfonic acids, such as benzene sulfonic acids carrying long-chain alkyl substituents (see below), are often employed as technical grade mixtures with different alkyl substituents and are thus properly spoken mixtures of different sulfonic acids. But also mixtures of structurally more different sulfonic acids can be used.

The observations made below in relation to preferred embodiments of features of the method of the invention apply not only individually per se, but also, more particularly, in any conceivable combination with one another.

Sulfonic acids are characterized by the functional group —$SO_3H$.

The organic moieties mentioned in the above definitions of the variables are collective terms for individual listings of the individual group members. The prefix $C_n$-$C_m$ Indicates in each case the possible number of carbon atoms in the group.

The term "alkyl" as used herein refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 1 to 6 ("$C_1$-$C_6$-alkyl"), 1 to 8 ("$C_1$-$C_8$-alkyl"), 1 to 10 ("$C_1$-$C_{10}$-alkyl") or 1 to 20 ("$C_1$-$C_{20}$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof. $C_1$-$C_{20}$-Alkyl is additionally also, for example, undecyl, dodecyl, tridecyl, tetradecyl, pentadecyl, hexadecyl, heptadecyl, octadecyl, nonadecyl, ecosyl and positional isomers thereof. $C_{12}$-Alkyl is dodecyl and positional isomers thereof. $C_8$-$C_{20}$-Alkyl is a saturated straight-chain or branched hydrocarbon radical having 8 to 20 carbon atoms, such as octyl, nonyl, decyl, undecyl, dodecyl, tridecyl, tetradecyl, pentadecyl, hexadecyl, heptadecyl, octadecyl, nonadecyl, eicosyl and positional isomers thereof. $C_{10}$-$C_{14}$-Alkyl is a saturated straight-chain or branched hydrocarbon radical having 10 to 14 carbon atoms, such as decyl, undecyl, dodecyl, tridecyl, tetradecyl and positional isomers thereof.

Preferably, $R^1$ is selected from phenyl which carries 2 or 3 $C_1$-$C_4$-alkyl substituents or one $C_8$-$C_{20}$-alkyl substituent, and naphthyl.

In a specific embodiment, $R^1$ is selected from phenyl which carries one $C_8$-$C_{20}$-alkyl substituent, very specifically one $C_{10}$-$C_{14}$-alkyl substituent.

In an alternative specific embodiment, $R^1$ is selected from phenyl which carries 2 or 3 $C_1$-$C_4$-alkyl substituents, very specifically 2 or 3 methyl substituents. Preferably, one or two of these $C_1$-$C_4$-alkyl substituents are bound ortho to the $SO_3H$ group.

Preferably, the at least one sulfonic acid catalyst is used in a total amount of from 0.01 to 1 mol-%, preferably from 0.02 to 0.3 mol-%, in particular from 0.03 to 0.2 mol-%, specifically from 0.1 to 0.2 mol-%, relative to the amount of 3-methylbut-3-en-1-ol used.

3-Methylbut-3-en-1-ol and 3-methylbut-2-enal are preferably used in a weight ratio of from 5:1 to 1:5, preferably from 2:1 to 1:2, in particular from 1.5:1 to 1:1.5 and especially about 1:1. "About" means to include possible tolerances, such as weighing errors and the like.

The reaction of prenal and isoprenol to dehydro rose oxide comprises the formation of water. It is supposed that the presence of water might facilitate the formation of double bond isomers of dehydro rose oxide via a hydration/dehydration step. Therefore, it is advantageous to remove the eliminated water in the course of the reaction, preferably permanently during the whole reaction. Removal of water can be carried out by any known means, e.g. by simple distillation. However, it is more preferred to use an entrainer. Thus, it is preferred to remove the water formed in the reaction of 3-methylbut-3-en-1-ol and 3-methylbut-2-enal by azeotropic distillation during the reaction. For practical reasons, it is preferred to carry out the reaction in a solvent which is an entrainer for water, or with other words, which can form an azeotrope with water, advantageously a minimum azeotrope.

Solvents which form minimum azeotropes with water are known to those skilled in the art and are, for example, ethanol, cyclohexane, benzene, toluene, ethylbenzene, the xylenes, ethyl acetate etc.

Among these, preference is given to cyclohexane, benzene, toluene, ethylbenzene, ortho-xylene, meta-xylene, para-xylene and mixtures thereof. Specifically, toluene is used.

The reaction is preferably carried out at a temperature from 60 to 200° C., more preferably from 80 to 140° C.

The reaction is preferably carried out at a pressure of from 100 to 1200 mbar (the values being absolute pressure). In one preferred embodiment, the reaction is carried out at ambient pressure. As the reaction of prenal and isoprenol to dehydro rose oxide comprises the formation of water which is preferably removed, in a more preferred embodiment, the reaction is carried out at a pressure below ambient pressure in order to facilitate the removal of water; e.g. at a pressure of from 100 to 900 mbar, in particular from 300 to 900 mbar.

The reaction can be carried out in different ways. For example, the starting compounds isoprenol and prenal, the at least one sulfonic acid catalyst and optionally a solvent can be mixed, the mixture be brought to the desired temperature and pressure and the water formed removed, e.g. by simple distillation or by azeotropic distillation if an entrainer, especially a solvent forming a (minimum) azeotrope with water is used. When no more water can be removed, the reaction can be stopped, or, preferably, continued for some time to complete the reaction. The optimum duration of this after-reaction depends on several factors, such as batch size, reaction temperature, specific catalyst etc. and can be determined by those skilled in the art, e.g. by preliminary experiments.

It is however preferred to first bring a mixture of solvent (preferably a solvent which forms a minimum azeotrope with water; see above remarks) and catalyst (i.e. the at least one sulfonic acid) to the desired temperature and pressure and add then the starting compounds isoprenol and prenal. These may be added as a mixture or separately. In case of separate addition, they may be added simultaneously or successively, the simultaneous addition being preferred. The starting compounds may be added at once, i.e. In one portion, or, preferably, by and by, either portionwise or, preferably, continually. The optimum addition rate depends on several factors, such as batch size, amount of solvent used etc. Water is preferably removed from the beginning of its formation. This is preferably done by azeotropic distillation, especially by azeotropic distillation with the solvent used. When no more water can be removed, the reaction can be stopped, or, preferably, continued for some time to complete the reaction. The optimum duration of this after-reaction depends on several factors, such as batch size, reaction temperature, specific catalyst etc. and can be determined by those skilled in the art, e.g. by preliminary experiments.

The sulfonic acid catalyst can be added to the reaction neat Especially if the sulfonic acid is a solid and the reaction is carried out on a technical scale, for practical reasons, it may be however advantageous to introduce the sulfonic acid in dispersed form, e.g. as a suspension, emulsion or, preferably, as a solution. Suitable solvents are those which sufficiently disperse, especially dissolve, the sulfonic acid and do not negatively interfere with the reaction. For example, p-toluene sulfonic acid can be used in form of its aqueous solution. If the sulfonic acid is flowable, e.g. liquid or viscous, it is not necessary to use the acid in dispersed (dissolved) form, even on a technical scale.

After completion of the reaction, the obtained product can be isolated and purified by methods known in the art, e.g. by distillation, extraction and/or chromatography. For example, to separate the product from the catalyst, the reaction mixture is distilled, optionally under reduced pressure, to leave the catalyst as bottom product. The desired product can then be separated from unreacted starting compounds, if any, solvent and by-products by further distillation or rectification steps. Alternatively, the reaction mixture is neutralized with an aqueous base, such as aqueous NaOH, KOH or $Na_2CO_3$, the phases are separated, and if desired the organic phase is washed with water and/or brine. The desired product, which is in the organic phase, can be separated from unreacted starting compounds, if any, solvent and by-products by further distillation or rectification steps.

Further purification can be done, for example, by chromatographic methods.

The method of the invention yields dehydro rose oxide in high yields and selectivities. Moreover, the sulfonic acid catalyst does not interfere negatively with the reactors in which the reaction is generally carried out on technical scale, as it is not abrasive and much less corrosive than the catalysts of the state of the art.

The invention is now illustrated by the following, non-limiting examples.

EXAMPLES

Examples 1 to 7

A 0.75 L reactor equipped with a Dean-Stark-trap and a vacuum pump was charged with toluene (239 g) and p-toluene sulfonic acid (560 mg of a 65% solution in water, 2.11 mmol) and the solution was brought to 110° C. (ambient pressure). To this solution a mixture of 95.7 g (1.14 mol) prenal and 97.7 g (1.13 mol) of isoprenol was added by means of a syringe pump (0.7 mL/min). During the addition, water started to form and was removed into the Dean-Stark-trap. The heating temperature was kept at 120° C. At the end of the addition (i. e. after approximately 6 h) the temperature of the reaction mixture was 98° C. The reaction was heated for further 4 h after completion of the addition. After cooling to room temperature, 350 g of the reaction mixture (total mass of the mixture: 390 g) was distilled (bulb to bulb). The distillate (319 g) was analysed by GC. The yield of dehydro rose oxide (DHRO) was 48.5%, and the DHRO/NO ratio was 3.11 (in other words: 3.11:1).

The reaction was carried out analogously with the catalysts listed in the below table.

Table

| Example | Catalyst | Yield DHRO [%] | Yield NO [%] | Ratio DHRO/NO |
|---|---|---|---|---|
| 1 | ![](4-methylbenzenesulfonic acid) | 48.5 | 16.0 | 3.11 |
| 2 | ![](2,5-dimethylbenzenesulfonic acid) | 49.8 | 13.9 | 3.30 |
| 3 | ![](2,4,6-trimethylbenzenesulfonic acid) | 46.0 | 12.8 | 3.68 |
| 4 | *C$_{12}$H$_{25}$-C$_6$H$_4$-SO$_3$H | 49.6 | 14.3 | 3.57 |
| 5 | **C$_{12}$H$_{25}$-C$_6$H$_4$-SO$_3$H | 48.3 | 14.8 | 3.35 |
| 6 |  1-naphthalenesulfonic acid | 49.8 | 15.5 | 3.66 |
| 7 | 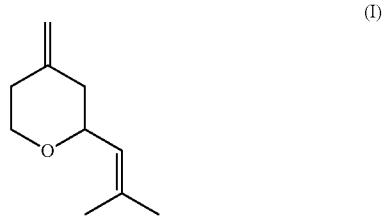 2-naphthalenesulfonic acid | 48.8 | 15.8 | 3.17 |

*Commercial product Marlon AS 3 from Sasol (http://www.sasoltechdata.com/Marketing-Brochures/Surfactants.pdf), which is an n-C$_{10}$-C$_{13}$-alkylbenzene sulfonic acid.
**Commercial product SBA NANSA ® anionic surfactants from Huntsman (http://www.huntsman.com/portal/page/portal/performance_products/Media%20Library/a_MC348531CFA3EA9A2E040EBCD2B6B7B06/Key%20markets_MC348531CFD2FA9A2E040EBCD2B6B7B06/Agrochemicals_MC348531CFFE4A9A2E040EBCD2B6B7B06/files/huntsman_agro_brochure_2010_final.pdf), which is branched C$_{12}$H$_{25}$-alkylbenzene sulfonic acid.

The invention claimed is:

1. A method for producing 4-methylene-2-(2-methylprop-1-enyl)tetrahydropyran of formula I

(I)

which method comprises reacting 3-methylbut-3-en-1-ol of formula II and 3-methylbut-2-enal of formula III (II)

(III)

in the presence of at least one sulfonic acid catalyst of formula $R^1$—$SO_3H$,
wherein $R^1$ is selected from phenyl that includes 2 or 3 $C_1$-$C_4$-alkyl substituents, phenyl that includes one $C_8$-$C_{20}$-alkyl substituent and optionally 1 or 2 $C_1$-$C_4$-alkyl substituents, and naphthyl, which optionally includes 1 or 2 $C_1$-$C_4$-alkyl substituents.

2. The method as claimed in claim 1, where $R^1$ is selected from phenyl that includes or 3 $C_1$-$C_4$-alkyl substituents or one $C_8$-$C_{20}$-alkyl substituent, and naphthyl.

3. The method as claimed in claim 2, where $R^1$ is selected from phenyl that includes one $C_8$-$C_{20}$-alkyl substituent.

4. The method as claimed in claim 3, where $R^1$ is selected from phenyl that includes one $C_{10}$-$C_{14}$-alkyl substituent.

5. The method as claimed in claim 2, where $R^1$ is selected from phenyl that includes 2 or 3 $C_1$-$C_4$-alkyl substituents.

6. The method as claimed in claim 5, where $R^1$ is selected from phenyl that includes 2 or 3 $C_1$-$C_4$-alkyl substituents, where 1 or 2 of these $C_1$-$C_4$-alkyl substituents are bound ortho to the $SO_3H$ group.

7. The method as claimed in claim 1, where the catalyst is present in an amount of from 0.01 to 1 mol-%, relative to the amount of 3-methylbut-3-en-1-ol present.

8. The method as claimed in claim 1, where 3-methylbut-3-en-1-ol and 3-methylbut-2-enal are present in a weight ratio of from 5:1 to 1:5.

9. The method as claimed in claim 1, where the reaction is carried out at a temperature from 60 to 200° C.

10. The method as claimed in claim 1, where the reaction is carried out at a pressure of from 100 to 1200 mbar.

11. The method as claimed in claim 1, where the reaction is carried out in a solvent which can form an azeotrope with water.

12. The method as claimed in claim 1, where the solvent is selected from cyclohexane, benzene, toluene, ethylbenzene, ortho-xylene, meta-xylene, para-xylene or mixtures thereof.

13. The method as claimed in claim 1, where water formed in the reaction of 3-methylbut-3-en-1-ol and 3-methylbut-2-enal is removed by azeotropic distillation during the reaction.

14. The method as claimed in claim 1, which comprises:
mixing the 3-methylbut-3-en-1-ol, the 3-methylbut-2-enal, the at least one sulfonic acid and optionally a solvent, to form a mixture, and bringing the mixture to a desired temperature and pressure, and removing water formed in the reaction, or bringing the at least one sulfonic acid in a solvent to a desired temperature and pressure, adding 3-methylbut-3-en-1-ol and 3-methylbut-2-enal, and removing the water formed in the reaction.

15. The method as claimed in claim 1, where the catalyst is present in an amount of from 0.03 to 0.2 mol-%, relative to the amount of 3-methylbut-3-en-1-ol present, the 3-methylbut-3-en-1-ol and 3-methylbut-2-enal are present in a weight ratio of from 2:1 to 1:2, the reaction is carried out at a temperature from 80 to 140° C., and a pressure of from 300 to 900 mbar.

16. The method as claimed in claim 15, where the reaction is carried out in a solvent selected from cyclohexane, benzene, toluene, ethylbenzene, ortho-xylene, meta-xylene, para-xylene or mixtures thereof, and water formed in the reaction of 3-methylbut-3-en-1-ol and 3-methylbut-2-enal is removed by azeotropic distillation during the reaction.

* * * * *